(12) United States Patent  
Nunley et al.

(10) Patent No.: US 8,308,729 B2  
(45) Date of Patent: Nov. 13, 2012

(54) ROD REDUCTION DEVICE

(75) Inventors: Pierce Nunley, Shreveport, LA (US); Michael Barrus, Ashburn, VA (US); Scott Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 42 days.

(21) Appl. No.: 12/996,874

(22) PCT Filed: Jun. 11, 2009

(86) PCT No.: PCT/US2009/047002  
§ 371 (c)(1), (2), (4) Date: Dec. 8, 2010

(87) PCT Pub. No.: WO2009/152302  
PCT Pub. Date: Dec. 17, 2009

(65) Prior Publication Data  
US 2011/0118791 A1    May 19, 2011

Related U.S. Application Data

(60) Provisional application No. 61/131,645, filed on Jun. 11, 2008, provisional application No. 61/086,957, filed on Aug. 7, 2008.

(51) Int. Cl.  
*A61B 17/88* (2006.01)

(52) U.S. Cl. ............... 606/86 A; 606/79; 606/99

(58) Field of Classification Search .......... 606/279, 606/86 A, 99  
See application file for complete search history.

(56) References Cited

U.S. PATENT DOCUMENTS

| 5,720,751 | A | 2/1998 | Jackson |
| 6,123,707 | A | 9/2000 | Wagner |
| 6,957,758 | B2 | 10/2005 | Aranyi |
| 2002/0052603 | A1 | 5/2002 | Nichols et al. |
| 2004/0267275 | A1 | 12/2004 | Cournoyer et al. |
| 2006/0025769 | A1 | 2/2006 | Dick et al. |
| 2006/0036254 | A1* | 2/2006 | Lim ................ 606/86 |
| 2006/0271050 | A1 | 11/2006 | Piza Vallespir |
| 2007/0093817 | A1 | 4/2007 | Barrus et al. |
| 2007/0213716 | A1 | 9/2007 | Lenke et al. |
| 2007/0270811 | A1 | 11/2007 | Dewey |
| 2007/0270867 | A1 | 11/2007 | Miller et al. |
| 2007/0282337 | A1 | 12/2007 | Garamszegi |
| 2008/0015601 | A1 | 1/2008 | Castro et al. |

OTHER PUBLICATIONS

International Search Report and Written Opinion issued by the U.S. Searching Authority in counterpart PCT Application No. PCT/US2009/047002, completed Jul. 27, 2009; mailed Aug. 3, 2009; 7 pages.

* cited by examiner

*Primary Examiner* — Ellen C Hammond  
(74) *Attorney, Agent, or Firm* — Carter, DeLuca, Farrell & Schmidt, LLP

(57) ABSTRACT

A rod reduction device includes a housing defining a longitudinal axis. The housing has first and second arms extending distally therefrom. The distal ends of the arms are configured to releasably attach to a bone anchor. An anvil is operatively associated with the first and second arms of the housing and translatable along the longitudinal axis for facilitating the insertion of a spinal rod into the bone anchor. The anvil and each arm are positionable between an open position and a closed position.

14 Claims, 11 Drawing Sheets

ROD REDUCTION DEVICE

CROSS-REFERENCE TO RELATED APPLICATIONS

The present application is a National Stage Entry of PCT/US2009/047002, which was filed Jun. 11, 2009, and claims the benefit of U.S. Provisional Application No. 61/131,645, which was filed Jun. 11, 2008 and U.S. Provisional Application No. 61/086,957, which was filed Aug. 7, 2008, the entire contents of which are incorporated herein by reference.

BACKGROUND

1. Technical Field

The present disclosure relates to orthopedic surgery devices for stabilizing and fixing the bones and joints of the body. Particularly, the present disclosure relates to a manually operated device for reducing a spinal rod into a bone anchor in a controlled, measured manner.

2. Description of Related Art

The spinal column is a complex system of bones and connective tissues that provides support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions.

There are various disorders, diseases and types of injury that the spinal column may experience in a lifetime. The problems may include but are not limited to scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to stabilize or eliminate motion at the intervertebral disc or joint. To achieve this, natural or artificial bone, along with a spacing device, replaces either part, or all of the intervertebral disc to form a rigid column of bone, which is stabilized by mechanical hardware.

The mechanical hardware used to immobilize the spinal column typically involves a series of bone screws/anchors and metal rods or plates. When the spine surgery is performed posteriorly, it is common practice to place bone anchors into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of a bone anchor and then securing that connecting rod in place can often require that the surgeon use a number of instruments and expend a great deal of time and effort. When bone anchors in several adjacent vertebrae are to be securely connected by a spinal rod, the repeated process of inserting the rod into the heads of the bone anchors and then securing the rod in place for each respective bone anchor can be difficult, tiresome and time consuming. Further, the alignment of the rod as it connects to each of the sequential bone anchors may require adjustment during the procedure and, therefore it is desirable that a device and method be provided by which the rod can be reduced into the head of each of the sequentially aligned bone anchors and, as necessary, easily adjusted so as to facilitate the process for the surgeon with minimal effort and loss of time.

SUMMARY

The present disclosure is directed to a rod reduction device including a housing defining a longitudinal axis and having first and second arms extending distally therefrom. The housing includes a housing bore extending longitudinally therethrough. The housing bore is configured to receive a driver for engaging a bone anchor. The rod reduction device is configured to engage the driver that advances the rod reduction device and the bone anchor into bone.

The first and second arms of the housing are positionable between a first position and at least one second position. The arms are parallel to each other in at least one position. The distal ends of the arms are configured to releasably attach to the bone anchor. The distal ends of the arms include at least one grasping feature for engaging the bone anchor.

An anvil is operatively associated with the first and second arms of the housing and is translatable along the longitudinal axis for facilitating the insertion of a spinal rod into the bone anchor. The anvil includes first and second bores for receiving the first and second arms of the housing. The first and second bores are parallel to each other. The anvil is positionable between a first position and at least one second position. The anvil is configured to position the arms to a parallel position upon moving the anvil a predetermined distance distally from the housing. The anvil includes an anvil bore extending longitudinally therethrough. The anvil bore is configured to receive the driver for engaging the bone anchor.

In one embodiment, the anvil includes an anvil post disposed at the distal end thereof.

In one embodiment, the rod reduction device includes a reduction screw that advances the anvil. In this embodiment, the reduction screw includes an engaging spool disposed on the distal end thereof, wherein the engaging spool is disposed in mechanical cooperation with an anvil head. The anvil head is coupled to the engaging spool via at least one interconnecting pin. A thrust bearing is operatively associated with the engaging spool and the anvil head, the thrust bearing being disposed therebetween. The anvil head has a contoured surface.

In another aspect of the present disclosure, a method for providing spinal support includes providing a rod reduction device having a housing defining a longitudinal axis and having first and second arms extending distally therefrom, wherein distal ends of the arms are configured to releasably attach to a bone anchor; and an anvil operatively associated with the first and second arms of the housing and translatable along the longitudinal axis for facilitating the insertion of a spinal rod into the bone anchor; wherein the anvil and each arm are positionable between a first position and at least one second position. The method further includes securing the rod reduction device to the bone anchor, placing the rod between the first and second arms of the housing, reducing the rod into the bone anchor with the rod reduction device, and locking the rod to the bone anchor. The method also includes mounting the at least one bone anchor and the at least one rod to at least one vertebral body.

In another aspect of the present disclosure, a method for providing spinal support includes providing a plurality of rod reduction devices, each rod reduction device including a housing defining a longitudinal axis and having first and second arms extending distally therefrom, wherein distal ends of the arms are configured to releasably attach to a bone anchor; and an anvil operatively associated with the first and second arms of the housing and translatable along the longitudinal axis for facilitating the insertion of a rod into the bone anchor; wherein the anvil and each arm are positionable between a first position and at least one second position; providing a plurality of bone anchors. The method further includes securing each rod reduction device to a bone anchor of the plurality of bone anchors, placing the rod between the first and second arms of each rod reduction device, sequentially reducing portions of the rod into the plurality of bone anchor with the rod reduction devices; and sequentially locking portions of the rod to the plurality of bone anchors.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION OF EMBODIMENTS

Figure 1A:
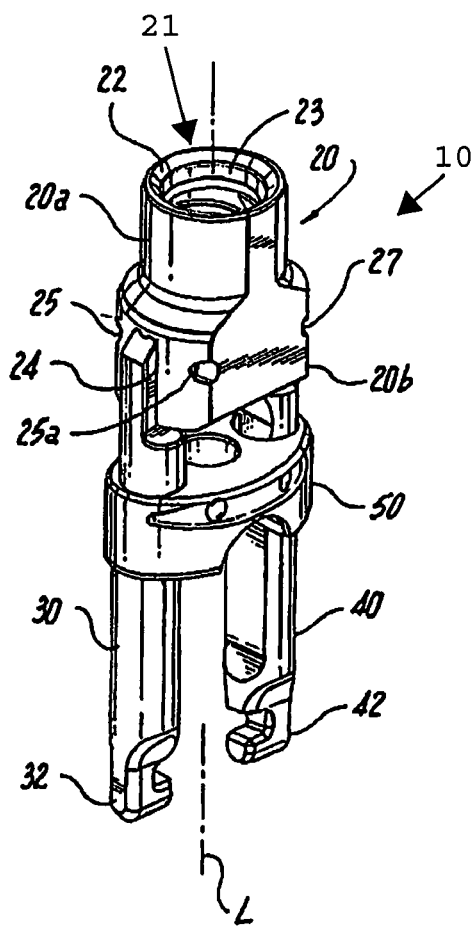
FIG. 1A is a perspective view of one embodiment of a rod reduction device in accordance with the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the device that is closer to the user and the term "distal" refers to the end of the device that is farther from the user. In the following description, well-known functions or constructions are not described in detail to avoid obscuring the present disclosure in unnecessary detail.

Referring now to the drawings, in which like reference numerals identify identical or substantially similar parts throughout the several views, FIG. 1A illustrates a rod reduction device 10. In accordance with the present disclosure, the rod reduction device 10 includes a housing 20 having first and second arms 30, 40 extending distally therefrom and an anvil 50 operatively associated with the first and second arms 30, 40.

With continued reference to FIG. 1A, the housing 20 defines a longitudinal axis "L" and includes a proximal end 20a and a distal end 20b. The proximal end 20a includes a top surface 22, which may be contoured, and a longitudinal opening 21. The housing 20 includes a housing bore 23 extending therethrough. The longitudinal opening 21 and the housing bore 23 may be engaged by a plurality of instruments "I" (e.g., a reduction screw 600 {FIGS. 2A and 2B} described in further detail hereinbelow). In addition, the housing 20 includes a first notch 24 and a second notch (not shown) that is substantially similar to the first notch 24, but is defined within the opposing side of the housing 20. The first notch 24 and the second notch are configured for receiving the respective first and second arms 30, 40. First and second channels 25, 27 are cut through the housing 20 transverse to the longitudinal axis "L" on opposing sides of the housing 20 for receiving a first arm pin 25a and a second arm pin 27a (FIG. 3A) respectively therethrough. The second arm pin 27a is the same as the first arm pin 25a and each is configured to support respective first and second arms 30, 40 relative to the housing 20. As such, the first and second arms 30, 40 can pivot relative to the housing 20.

Figure 1B:
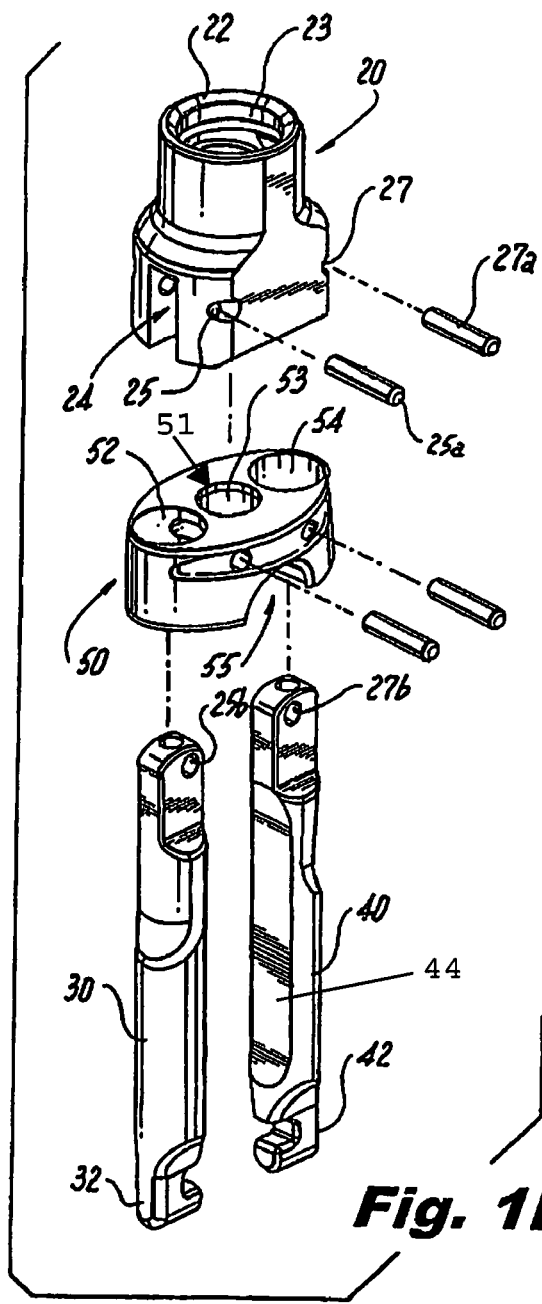
FIG. 1B is a perspective view, with parts separated, of the rod reduction device of FIG. 1A.

Referring now to FIGS. 1A-1B, the first arm 30 is positioned within the first notch 24 and the second arm 40 is positioned within the second notch. The first and second arms 30, 40 receive arm pins 25a, 27a through pin holes 25b, 27b disposed at the proximal end of arms 30, 40. The first and second arms 30, 40 are pivotally attached to the housing 20, wherein the arms 30, 40 may pivot through a predefined angle with respect to the housing 20. Accordingly, the arms 30, 40 are movable or repositionable throughout a plurality of positions including an open position and a closed position. At the distal end of each arm 30, 40 is a grasping feature 32, 42, which may be a hook or a claw disposed in mirror image with the opposing grasping feature 32, 42. Each grasping feature 32, 42 is configured to releasably attach to a complimentary mating feature on a bone anchor "B" (See FIGS. 3A-3B). Each arm 32, 42 includes an inwardly facing cut portion 44 for enabling the anvil 50 to readily translate therealong.

Figure 2A:
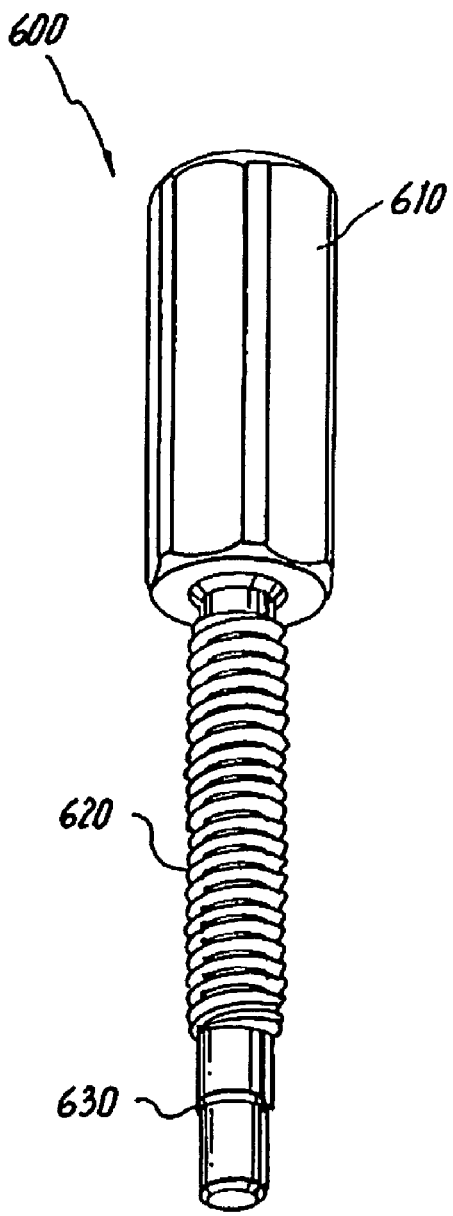
FIG. 2A is a perspective view of one embodiment of a reduction screw in accordance with the present disclosure.
Figure 2B:
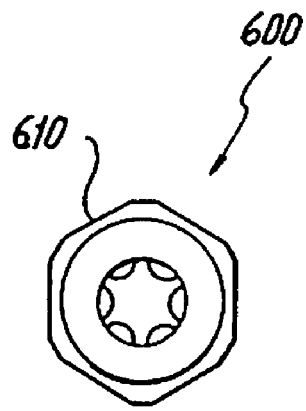
FIG. 2B is a top view of the reduction screw of FIG. 2A.
Figure 3A:
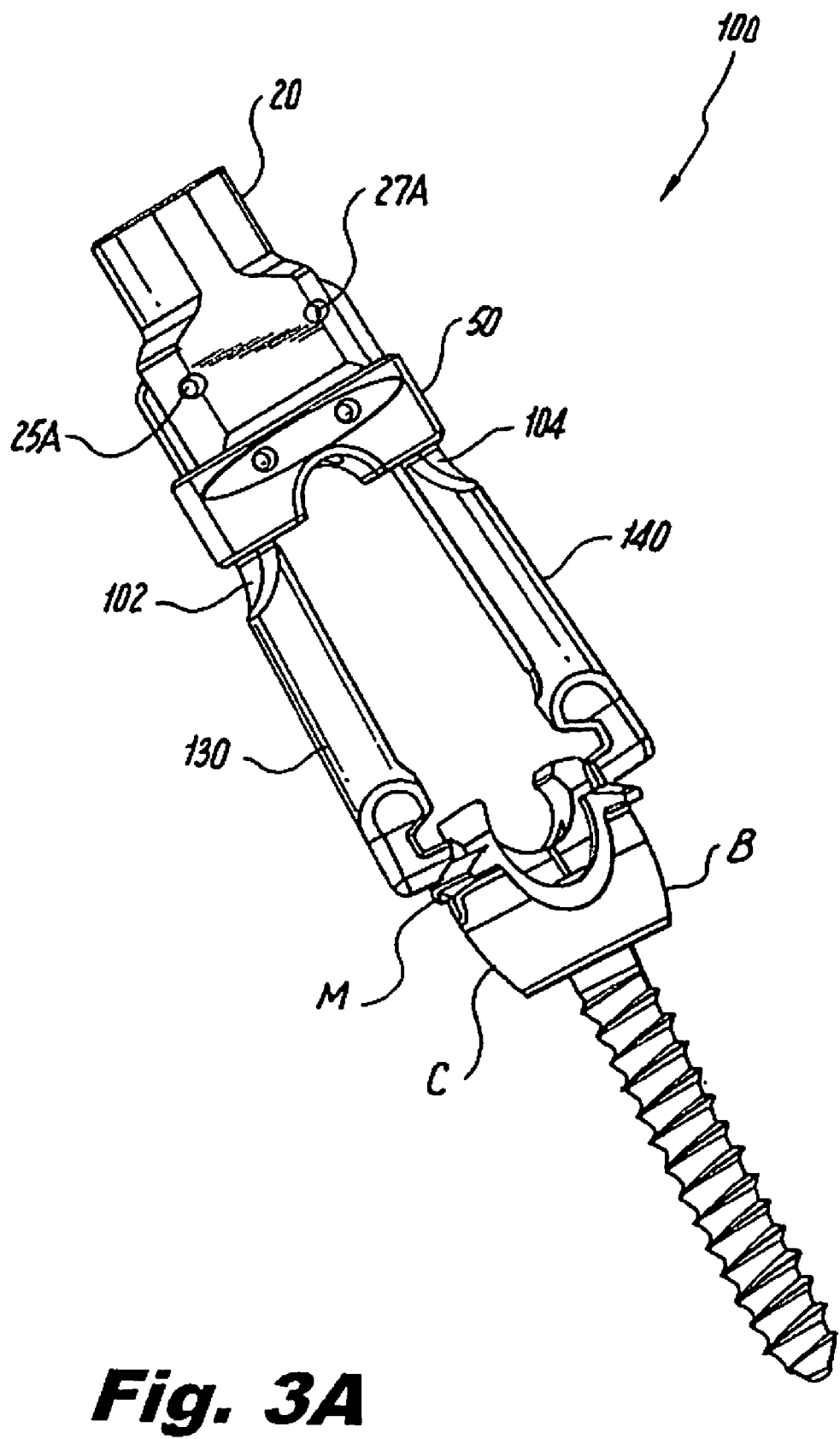
FIG. 3A is a perspective view of another embodiment of a rod reduction device shown in a first position prior to engaging a bone anchor assembly.
Figure 3B:
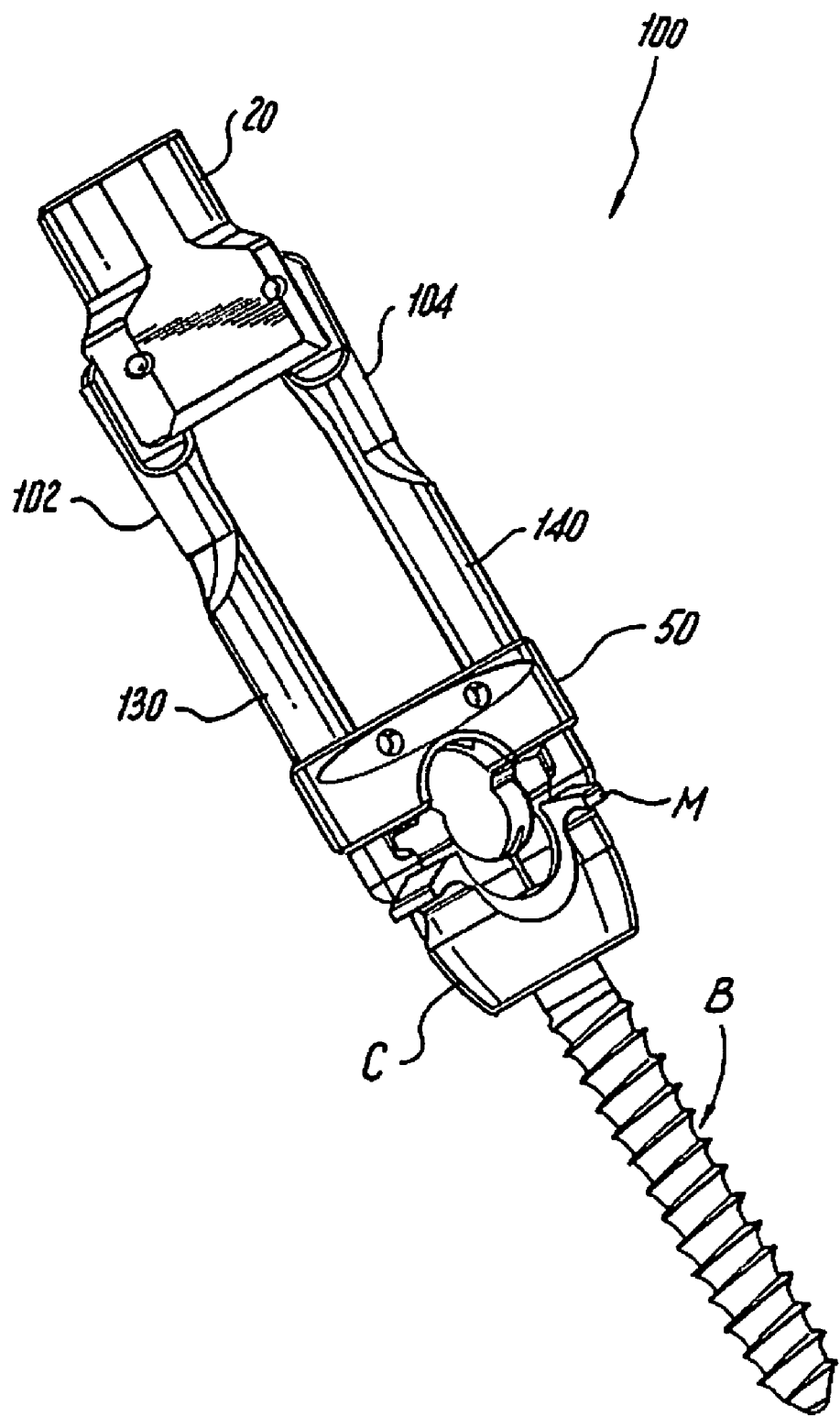
FIG. 3B a perspective view of the rod reduction device and the bone anchor assembly of FIG. 3A, the rod reduction device shown in a second position engaged with the bone anchor assembly.

Referring again to FIGS. 1A-1B, the anvil 50 includes parallel first and a second arm bores 52, 54 for translating along the first and second arms 30, 40 from the open position to the closed position and along the longitudinal axis "L" for facilitating the insertion of a spinal rod "R" (See FIG. 5) into the bone anchor "B" (See FIGS. 3A-3B). The anvil 50 includes a longitudinal opening 51 and an anvil bore 53 extending therethrough. The longitudinal opening 51 and the anvil bore 53 may be engaged by a plurality of instruments "I" (e.g., a reduction screw 600 {FIGS. 2A and 2B} described in further detail hereinbelow). An arcuate channel 55 is disposed along the distal end of the anvil 50 transverse to the longitudinal axis "L" for engaging a spinal rod "R." (See FIG. 5). In the open position, the arms 30, 40 are separated and the anvil 50 is disposed proximal to the housing 20. When the anvil 50 moves distally, the arms 30, 40 pivot toward each other, become parallel, and are positioned in the closed position. The transition of the anvil 50 and arms 30, 40 from open to closed positions occurs when the anvil 50 has translated distally from the housing 20 within the first quarter of the distance along the arms 30, 40 down the longitudinal axis measured from the housing 20 to the distal ends of the arms 30, 40. In particular, the rod reduction device 10 is considered to be "closed" when the arms 30, 40 are parallel and the anvil 50 has translated approximately 25% away from the housing 20. When the rod reduction device 10 is in its closed position, the grasping features 32, 42, e.g. the hook or claw geometry, engage complimentary mating recesses "M" of the bone anchor "B," (FIGS. 3A-3B) removably attaching the rod reduction device 10 to the bone anchor "B." When the rod reduction device 10 is removably attached to the bone anchor "B", the two pieces act as a single unit and may be collectively introduced into the anatomy.

As illustrated in FIGS. 3A-3B, another embodiment of a rod reduction device 100 is shown in the open position engaging the bone anchor "B." Rod reduction device 100 is substantially similar to rod reduction device 10, but rod reduction device 100 includes first and second outwardly facing cut portions 102, 104 disposed on the proximal ends of first and second arms 130, 140 so that the anvil 50 may translate therealong from the open position (FIG. 3A) to the closed position (FIG. 3B).

Figure 4:
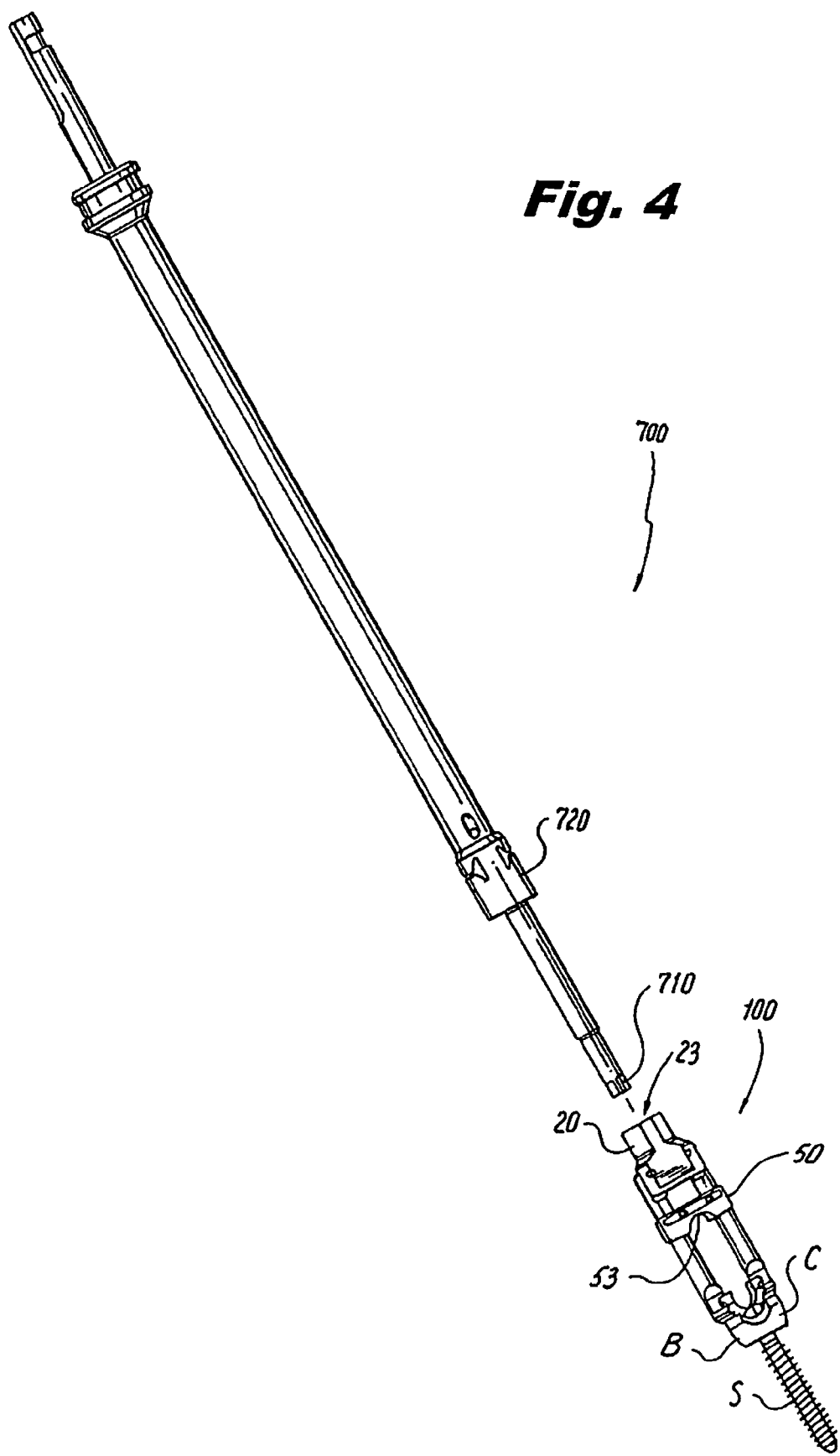
FIG. 4 is a perspective view of one embodiment of a driver positioned to engage the rod reduction device and the bone anchor assembly of FIGS. 3A-3B.

As shown in FIG. 4, a driver 700 with a driving end 710, e.g., a hexalobular end, may be passed through the housing bore 23 disposed longitudinally through the housing 20 and through the anvil bore 53 disposed longitudinally through the anvil 50. In addition to the driving end 710, the driver 700 includes a sleeve 720 configured to engage housing 20. When the sleeve 720 engages the housing 20, the driver 700 can transmit torque to the rod reduction device 10 and the bone anchor "B." In operation, the user may employ driver 700 to insert the bone anchor "B" into the bone and to reduce the spinal rod "R" into the in the saddle "X" of the bone anchor "B."

In one exemplary method of operation, the user positions the bone anchor "B" close to a bone and places the sleeve 720 over the proximal end 20a of the housing 20. Moreover, the user passes driving end 710 through the housing bore 23 and the anvil bore 53 until the driving end 710 engages a shaft portion "S" of the bone anchor "B." Then, a torsional force is applied to the driver 700. Upon application of such torsional force, the rod reduction device 10 rotates along with the bone anchor "B" to advance the bone anchor "B" distally into the bone.

Figure 5:
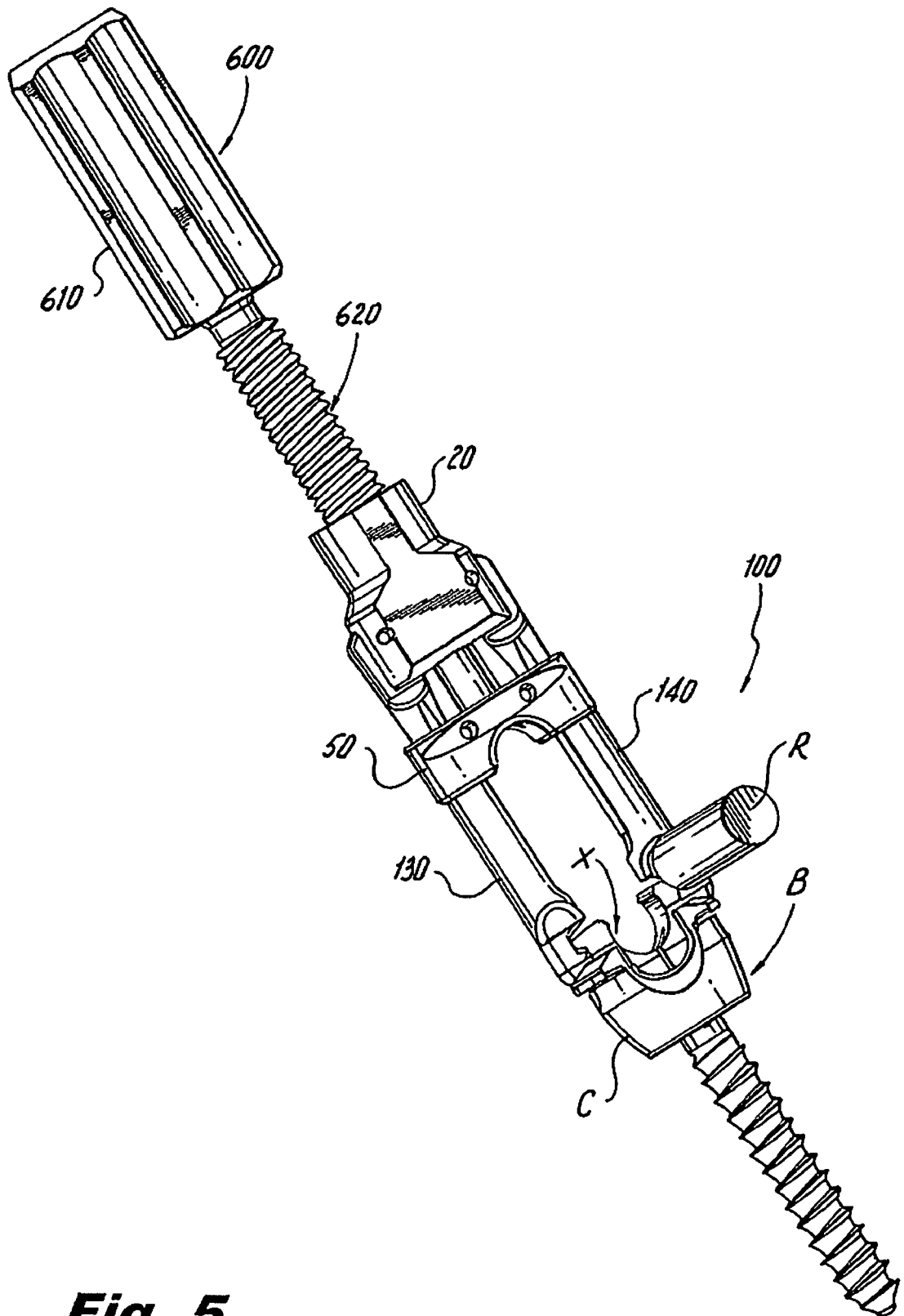
FIG. 5 is perspective view of the reduction screw of FIGS. 2A-2B engaging the rod reduction device and the bone anchor assembly of FIGS. 3A-3B.

Once the bone anchor "B" is advanced to its desired position, the driver 700 and/or driver tube 800 may be removed and the reduction screw 600 (FIGS. 2A-2B) may be inserted through the housing bore 23 (FIG. 5) and the anvil bore 53. As shown in FIGS. 2A-2B and 5, the reduction screw 600 has a head 610 disposed on the proximal end thereof for driving the reduction screw 600, a threaded portion 620 on the distal end for advancing the reduction screw 600 through the housing bore 23 and the anvil bore 53, and a shoulder 630 positioned distally of the threaded portion 620. From the illustration in FIG. 5, the spinal rod "R" may also be introduced between the two arms 130, 140 of the rod reduction device 100 and above the saddle "X" of the bone anchor "B". The threads of the reduction screw 600 engage threads on the inside of the housing bore 23 (see FIG. 1A) such that when a torsional force is applied to the reduction screw 600 a controlled and measurable incremental linear advancement of the reduction screw 600 occurs. As the reduction screw 600 is advanced, it passes through the anvil bore 53 until the shoulder 630 engages on the anvil 50. At this point, shoulder 630 rests on the anvil 50 and the reduction screw 600 is ready to drive anvil 50. Further distal advancement of the reduction screw 600 drives anvil 50 distally along the first and second arms 30, 40. Eventually, the arcuate channel 55 of the anvil 50 engages spinal rod "R." Once the arcuate channel 55 engages spinal rod "R", further distal advancement of reduction screw 600 causes the anvil 50 to drive spinal rod "R" distally into the saddle "X" of the bone anchor "B".

Figure 6:
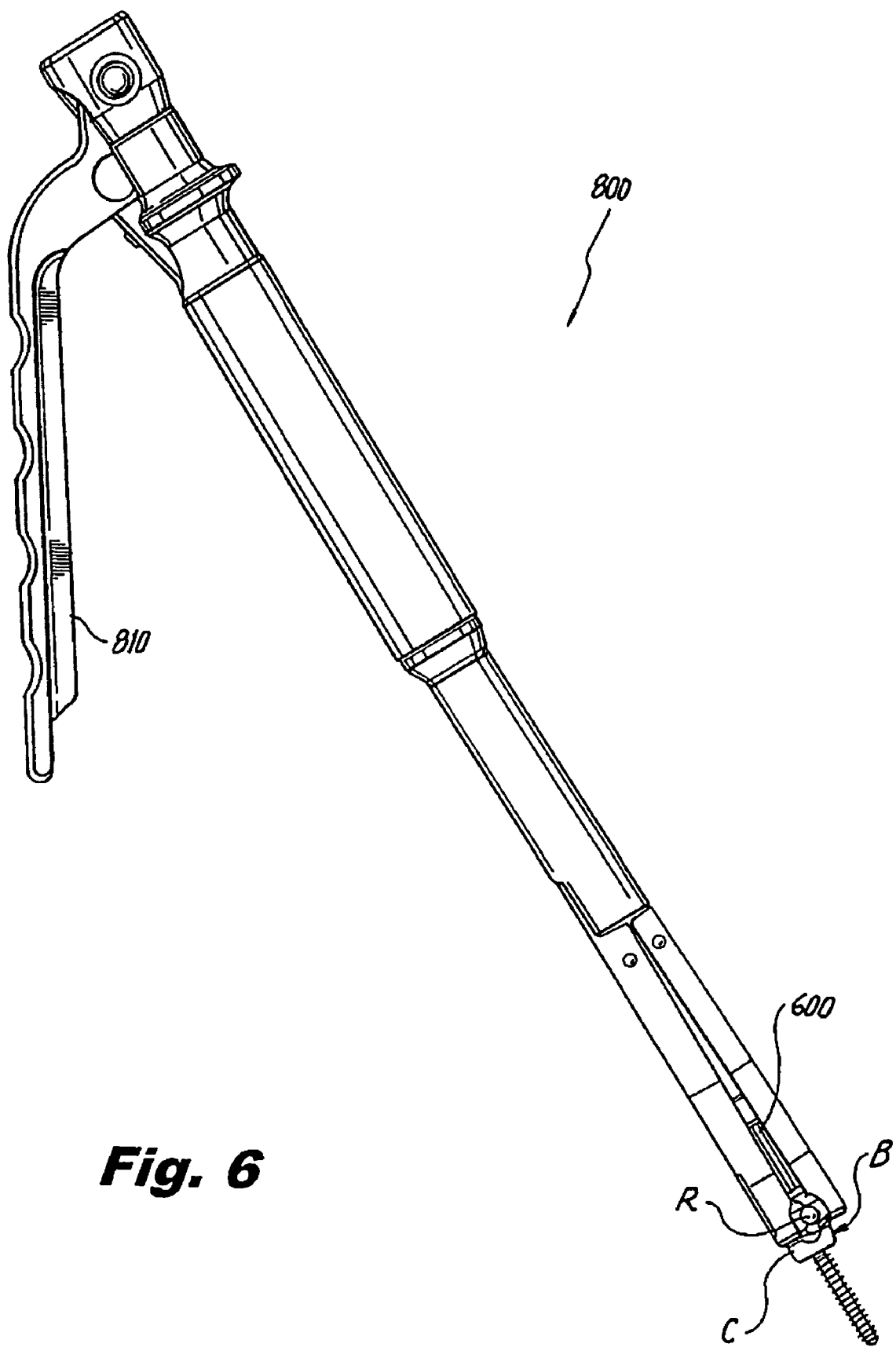
FIG. 6 is a perspective view of a locking instrument engaging the assembly shown in FIG. 5.

After the spinal rod "R" has been fully reduced, or seated in the saddle "X" of the bone anchor "B", the driving tube 800, a locking instrument (FIG. 6) may be placed overtop the entire assembly. Squeezing the lever 810 of the driving tube 800 causes it to engage the bone anchor "B" and pull up on a coupling "C" of the bone anchor "B" while pushing down on the reduction screw 600 and spinal rod "R" thereby fully locking the spinal rod "R" into the bone anchor "B" without applying any force to the patient. Releasing the lever 810 disengages the driving tube 800 from the bone anchor "B" so the driving tube 800 may be removed. The reduction screw 600 may then be unscrewed, the anvil 50 retracted and the rod reduction device 10, 100 may be disassembled from the bone anchor "B." The driving tube 800 may fully or partially lock the bone anchor "B" onto the spinal rod "R." The spinal rod "R" may be partially locked (i.e., reducing the spinal rod "R" in the saddle "X" {the spinal rod "R" can move transverse to the longitudinal axis "L"}) or fully locked (i.e., pulling the coupling "C" up to the saddle "X" after the spinal rod "R" is reduced) to the bone anchor "B" in order to facilitate adjustment of adjacent bone anchors "B" along the spinal rod "R." Constructs having multiple bone anchors "B" along the spinal rod "R" are contemplated. The driving tube 800 may be used to lock one or more spinal rods "R" after assembling one or more completed spinal rod "R" and bone anchor "B" constructs. After one or more spinal rods "R" are reduced into one or more bone anchors "B" and adjusted for proper placement, each spinal rod "R" and each bone anchor "B" can be fully locked into place as described hereinabove. Accordingly, each spinal rod "R" and bone anchor "B" construct may be partially or fully locked (individually or collectively) using the driving tube 800 as described hereinabove. Thus, the bone anchor "B" and spinal rod "R" constructs may provide permanent spinal support to the patient.

Figure 7:
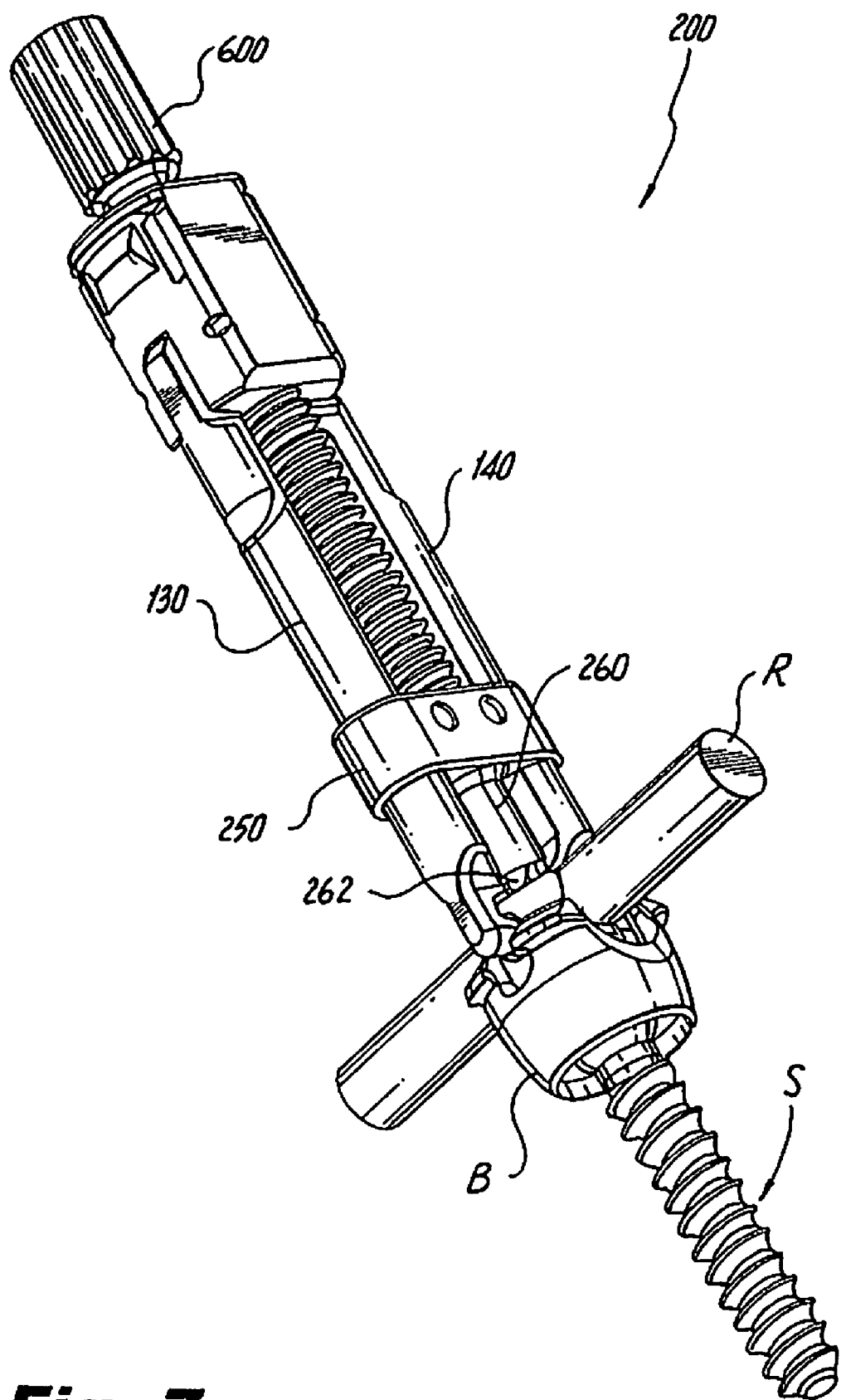
FIG. 7 is a perspective view of one embodiment of a rod reduction device in combination with the reduction screw of FIGS. 2A-2B and the bone anchor of FIGS. 3A-6, illustrating a post with a hexalobular end attached to the distal side of an anvil of the rod reduction device.
Figure 8:
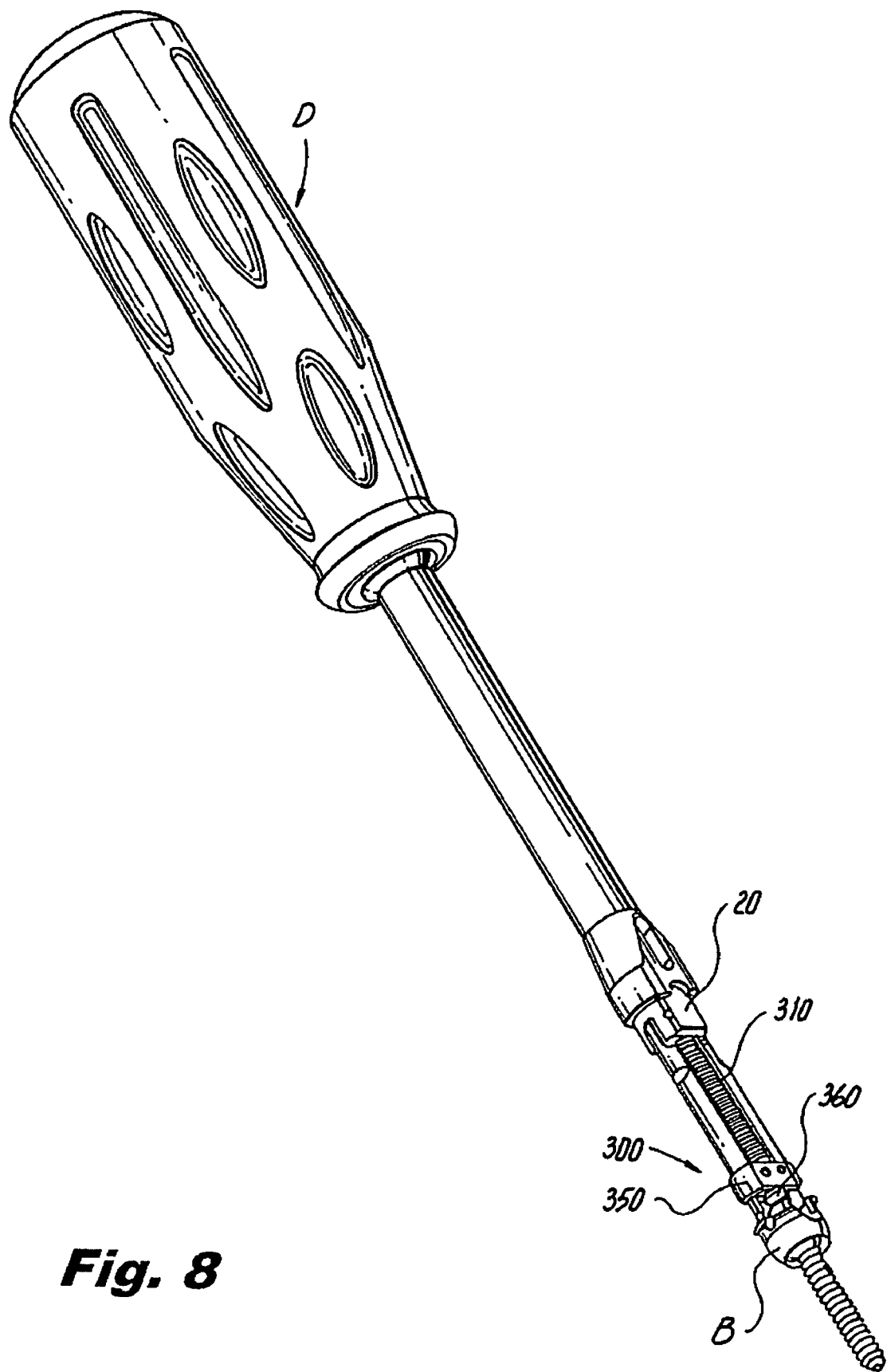
FIG. 8 is a perspective view of a driving instrument assembled to another embodiment of a rod reduction device and the bone anchor of FIGS. 3A-7.

In another embodiment of the rod reduction device 200 (FIG. 7), the anvil 250 is configured with an anvil post 260 disposed on the distal end thereof. The anvil post 260 has a hexalobular distal end 262. This embodiment of the rod reduction device 200 allows the anvil 250 to be moved distally to secure the arms 130, 140 to the bone anchor "B' while the hexalobular distal end 262 mates with the screw shank "S" of the bone anchor "B." Then, a driving instrument "D", such as that shown in FIG. 8, may be used to drive the screw shank "S" of the bone anchor "B" into bone from a proximal end of the driving instrument "D." The driving instrument "D" includes a distal end configured to engage the housing 20 and transmit torque to the rod reduction device 300 and to the bone anchor "B" attached to rod reduction device 300. In operation, the user may implant bone anchor "B" into bone before or after reducing the spinal rod "R" into the bone anchor saddle "X." In order to implant bone anchor "B," the user first places the distal end of the driving instrument "D" over the housing 20 and then rotates the driving instrument "D" while advancing the driving instrument "D" distally. During rotation, the distal end of driving instrument "D" transmits the torque to the rod reduction device 300 and the bone anchor "B." Consequently, the bone anchor "B" is incrementally introduced into the bone.

Before or after implanting the bone anchor "B" into the bone, the user may reduce spinal rod "R" into the bone anchor saddle "X". To achieve spinal rod reduction, the anvil post 260 of anvil 250 is retracted proximally and a spinal rod "R"

is placed between the arms 130, 140 of the rod reduction device 200. The user then rotates the reduction screw 600 about longitudinal axis "L," thereby driving anvil post 260 distally. While the anvil post 260 moves distally, the hexalobular distal end 262 of the anvil post 260 urges the spine rod "R" distally, reducing the spinal rod "R" into the bone anchor "B."

Figure 9:
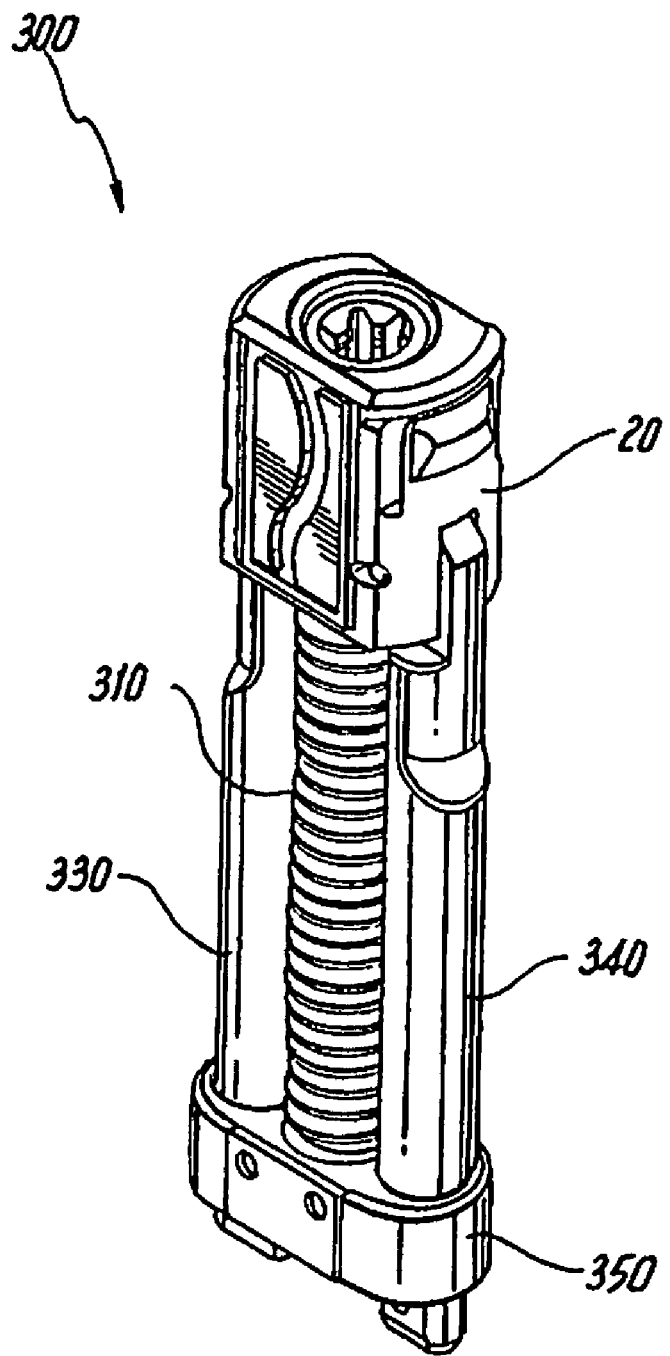
FIG. 9 is a perspective view of the rod reduction device of FIG. 8.

An alternative embodiment of the rod reduction device 300 (FIGS. 8, 9 and 10) is substantially similar to the embodiments of the rod reduction devices described above. However, rod reduction device 300 includes a reduction screw 310 disposed in mechanical cooperation with the housing 20 and an anvil 350. The reduction screw 310 has an engaging spool 320 at a distal end thereof for cooperation with interconnecting pins 330a, 330b and an anvil head 360. The engaging spool 320 is substantially cylindrical with an annular channel 322 constructed about the center. The anvil 350 has an anvil bore 352 adapted to receive the reduction screw 310 including the engaging spool 320, a thrust bearing 370, and the anvil head 360. The engaging spool 320 and anvil head 360 are configured to interconnect, being partially separated by the thrust bearing 370 sandwiched between the underside of the anvil head 360 and the distal end of the engaging spool 320. Furthermore, the engaging spool 320, the anvil head 360 and the anvil 350 are all interconnected via the interconnecting pins 330a, 330b.

Figure 10:
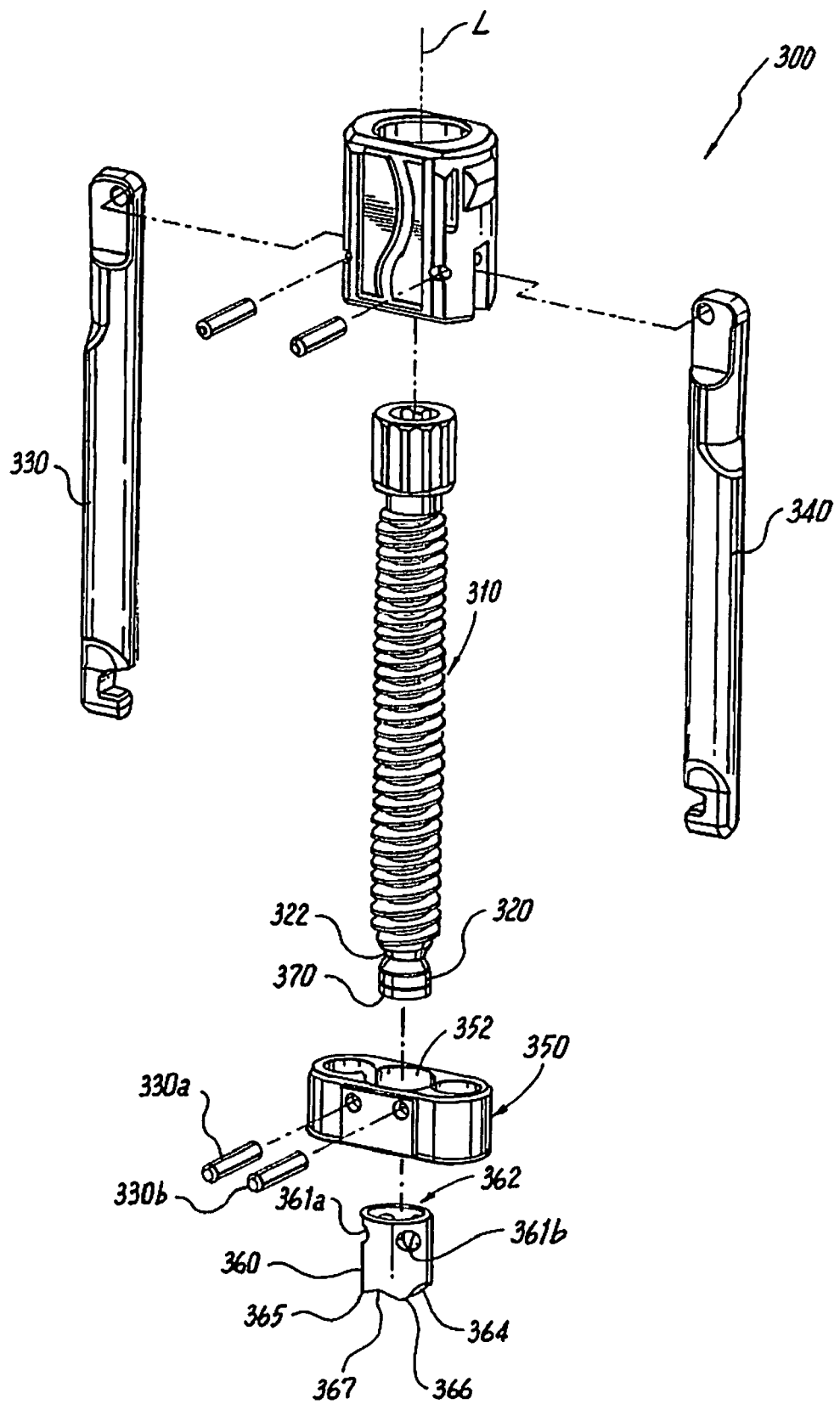
FIG. 10 is a perspective view, with parts separated, of the rod reduction device of FIGS. 8-9.

As shown in FIG. 10, the anvil head 360 has a substantially cylindrical body with a cavity 362 constructed partially therethrough beginning at the proximal end for receiving the thrust bearing 370 and a portion of the engaging spool 320. In addition, the anvil head 360 has a contoured surface 364 at the distal end. The contoured surface 364 has two protrusions 365, 366, both of which are symmetrically disposed transverse to the longitudinal axis "L" and are configured in a spaced apart relation relative to the centerline of the anvil head 360. A parabolic channel 367 is defined by the interior walls of the two protrusions 365, 366 and is constructed to engage a spinal rod "R." This contoured surface 364 may be substantially "v-shaped" for providing better contact with the spinal rod "R." Furthermore, the anvil head 360 can have notches 361a, 361b, disposed in the cylindrical wall for interconnecting the engaging spool 320, the anvil head 360, and the anvil 350 via the two interlocking pins 330a, 330b. Further still, the anvil head 360 may be made from a hard material for limiting deformation and providing increased surface-to-surface contact with the spinal rod "R" (See FIG. 7).

In operation, the threads of the reduction screw 310 engage the threads on the inside of the housing bore 23 such that when a torsional force is applied to the reduction screw 310 a controlled and measurable incremental linear advancement of the reduction screw 310 occurs. As the reduction screw 310 is advanced, the anvil head 360 connected thereto translates with the anvil 350 until it contacts the spinal rod "R" while simultaneously manipulating the arms 330, 340 into the closed position. As the anvil head 360 approaches the spinal rod "R," the parabolic channel 367 defined on the distal surface of the anvil head 362, e.g. the v-shaped surface, contours the spinal rod "R." The thrust bearing 370 translates the torsional force into thrust force along the longitudinal axis "L" and begins the advancement of the spinal rod "R." Further advancement of the reduction screw 310 reduces the spinal rod "R" into the bone anchor saddle "X." In this embodiment, the proximal surface of the reduction screw 310 may recess below the top surface of the housing 20 about 0.020 inches. This additional translation enables further compression of the anvil head 362 on the spinal rod "R."

Alternatively, and in addition to, a driver tube 800 (FIG. 6) may be removably attached to the housing 20 and a similar torsional force will advance the rod reduction device and bone anchor "B" as a single unit. Any number of prior art handles may be attached to the driver 700 or driver tube 800 in order to obtain the necessary mechanical advantage to aid in applying the torsional force. It is contemplated that other techniques and/or instruments known in the art may be utilized to install the bone anchor.

In use, any of the embodiments of the rod reduction devices disclosed in the present disclosure may be employed to reduce the spinal rod "R" in the saddle "X" of the bone anchor "B." This spinal rod reduction may occur before or after implanting the bone anchor "B" to a bone. To insert the bone anchor "B" into the bone, the user may utilize driving instrument "D" or any other suitable instrument.

The user may also reduce the spinal rod "R" with any disclosed rod reduction devices. Regardless of the specific embodiment used, the grasping features 32, 42 of each arm (e.g., 30 and 40) should engage the mating features "M" of the bone anchor "B." Then, the user translates the anvil (e.g., 50 or 250) distally along the first and second arms (e.g., 30 and 40) until the arms reach the closed position, thereby securing the rod reduction device to the bone anchor "B". After or before attaching the rod reduction device to the bone anchor "B," the user places the spinal rod "R" between the first and second arms (e.g., 30 and 40). Once the first and second arms (e.g., 30 and 40) have been placed in the second position, further distal advancement of the anvil (e.g., 50) urges the spinal rod "R" into the saddle "X" of the bone anchor "R." Optionally, the user may lock the spinal rod "R" to the bone anchor "B" with a set screw (not shown).

In another exemplary method of operation, the user may utilize multiple rod reduction devices (e.g, 100, 200, or 300) in a single surgery to reduce a single spinal rod "R" into multiple bone anchors "R." This spinal rod reduction may occur before or after implanting the bone anchor "B" to a bone. In any event, during this operation, the user sequentially secures each rod reduction device to a bone anchor. After or before attaching the rod reduction devices to the bone anchors "B," the user places the spinal rod "R" between the first and second arms (e.g., 30 and 40) of each rod reduction device. Then, the user sequentially manipulates each rod reduction device (as discussed above) to selectively reduce portions of the spinal rod "R" into each bone anchor "B." At the end, the spinal rod "R" would be reduced into the saddles "X" of each bone anchor "R." After reducing the spinal rod "R" into the bone anchors "B," the user may sequentially lock the spinal rod "R" to each bone anchor "B" with set screws (not shown)

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

What is claimed is:

1. A rod reduction device, comprising:
a housing defining a longitudinal axis and having first and second arms extending distally therefrom, wherein distal ends of the arms are configured to releasably attach to a bone anchor; and
an anvil operatively associated with the first and second arms of the housing and translatable along the longitudinal axis for facilitating the insertion of a spinal rod into the bone anchor, the anvil including an anvil body and an anvil post, the anvil post extending distally from a distal end of the anvil body, the anvil post including a distal surface that is engageable with the spinal rod to urge the spinal rod into the bone anchor when the arms of the housing are attached to the bone anchor, the anvil post being positioned between the arms of the housing in spaced apart relationship with the arms such that a gap is defined between the anvil post and each of the arms;
wherein the anvil and each arm are positionable between a first position and at least one second position.

2. The rod reduction device of claim 1, wherein the anvil includes first and second bores for receiving the first and second arms of the housing.

3. The rod reduction device of claim 1, wherein the arms are substantially parallel to each other in at least one position.

4. The rod reduction device of claim 1, wherein the distal ends of the arms include at least one grasping feature for engaging the bone anchor.

5. The rod reduction device of claim 1, wherein the anvil is configured to position the arms to a parallel position upon moving the anvil a predetermined distance distally from the housing.

6. The rod reduction device of claim 1, wherein the rod reduction device is configured to engage a driver that advances the rod reduction device and the bone anchor into bone.

7. The rod reduction device of claim 1, further comprising a reduction screw that advances the anvil.

8. The rod reduction device of claim 7, wherein the reduction screw includes an engaging spool disposed on the distal end thereof, wherein the engaging spool is disposed in mechanical cooperation with an anvil head.

9. The rod reduction device of claim 8, wherein the anvil head is coupled to the engaging spool via at least one interconnecting pin.

10. The rod reduction device of claim 8, further comprising a thrust bearing operatively associated with the engaging spool and the anvil head, the thrust bearing being disposed therebetween.

11. The rod reduction device of claim 8, wherein the anvil head has a contoured surface.

12. The rod reduction device of claim 1, wherein the first and second arms are hingedly connected to the housing.

13. A method for providing spinal support, comprising the steps of:
providing a rod reduction device, comprising:
a housing defining a longitudinal axis and having first and second arms extending distally therefrom, wherein distal ends of the arms are configured to releasably attach to a bone anchor; and
an anvil operatively associated with the first and second arms of the housing and translatable along the longitudinal axis for facilitating the insertion of a spinal rod into the bone anchor, the anvil including an anvil body and an anvil post, the anvil post extending distally from a distal end of the anvil body, the anvil post including a distal surface that is engageable with the spinal rod to urge the spinal rod into the bone anchor when the arms of the housing are attached to the bone anchor, the anvil post being positioned between the arms of the housing in spaced apart relationship with the arms such that a gap is defined between the anvil post and each of the arms;
wherein the anvil and each arm are positionable between a first position and at least one second position;
engaging the at least one rod with the distal surface of the anvil post;
reducing at least one rod into at least one bone anchor;
adjusting the at least one rod; and
locking the at least one rod to the bone anchor.

14. The method of claim 13, further comprising the step of:
mounting the at least one bone anchor and the at least one rod to at least one vertebral body.

* * * * *